United States Patent [19]

Hampel

[11] Patent Number: 4,975,933
[45] Date of Patent: Dec. 4, 1990

[54] BOW-TIE X-RAY FILTER ASSEMBLY FOR DUAL ENERGY TOMOGRAPHY

[75] Inventor: Willi W. Hampel, South Milwaukee, Wis.

[73] Assignee: General Electric Company, Milwaukee, Wis.

[21] Appl. No.: 498,409

[22] Filed: Mar. 26, 1990

[51] Int. Cl.$^5$ .............................................. G21K 3/00
[52] U.S. Cl. .......................................... 378/5; 378/18; 378/156
[58] Field of Search .............................. 378/5, 18, 156

[56] References Cited

U.S. PATENT DOCUMENTS 4,288,695  9/1981  Walters et al. ........................... 378/5
4,399,550  8/1983  Hauck et al. ............................. 378/5

Primary Examiner—Craig E. Church
Attorney, Agent, or Firm—Quarles & Brady

[57] ABSTRACT

A polymer attenuation filter in a CT machine is mounted at its center and allowed to expand freely at its ends to prevent cracking of the filter as it expands with temperature and after it becomes brittle with x-ray exposure. Vertical expansion of the filter at its center is accommodated by a stress relief hole cut between the center fastening points. Relatively greater horizontal expansion is accommodated by means of spring clamping. Difference in expansion between a metallic strip filter and its support is accommodated by tightly affixing the ends of the filter to the support so that the metallic strip is always under tension and cannot buckle.

6 Claims, 2 Drawing Sheets

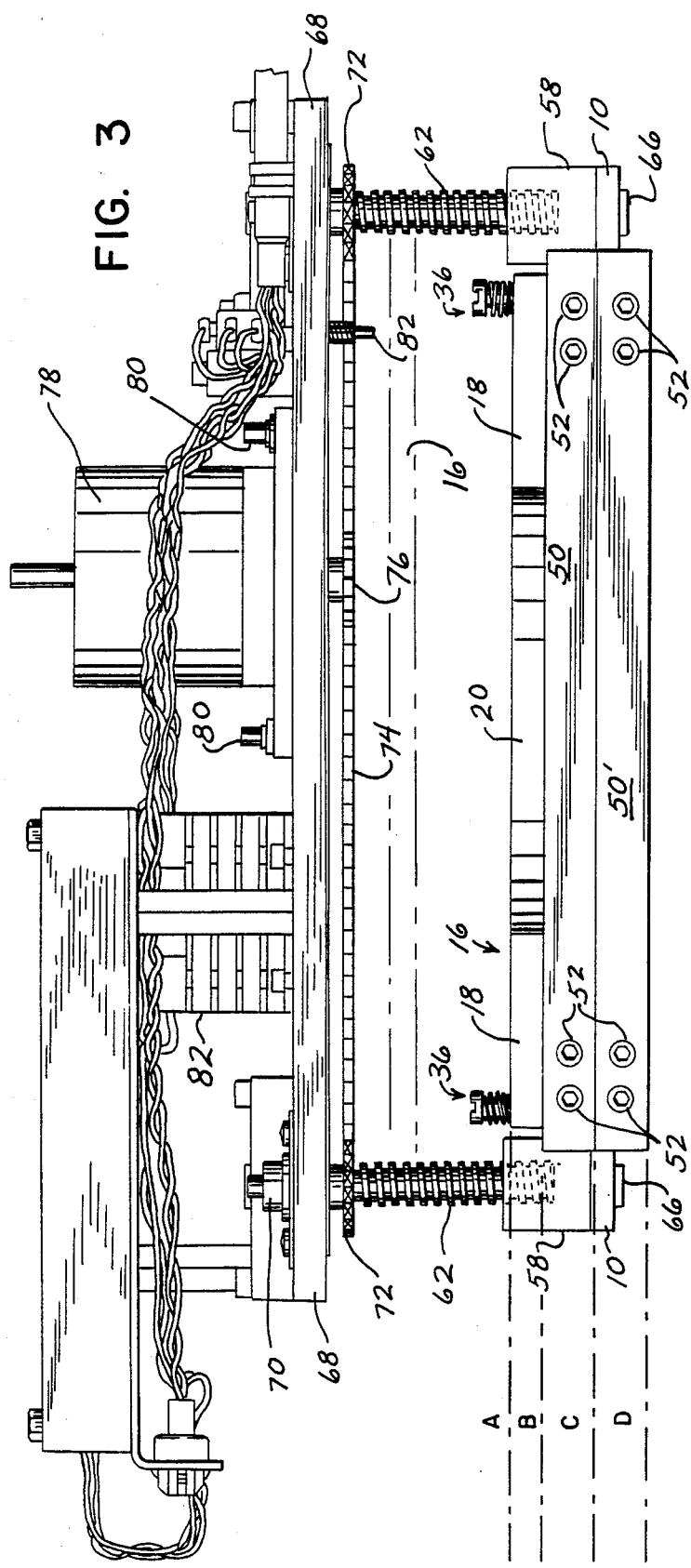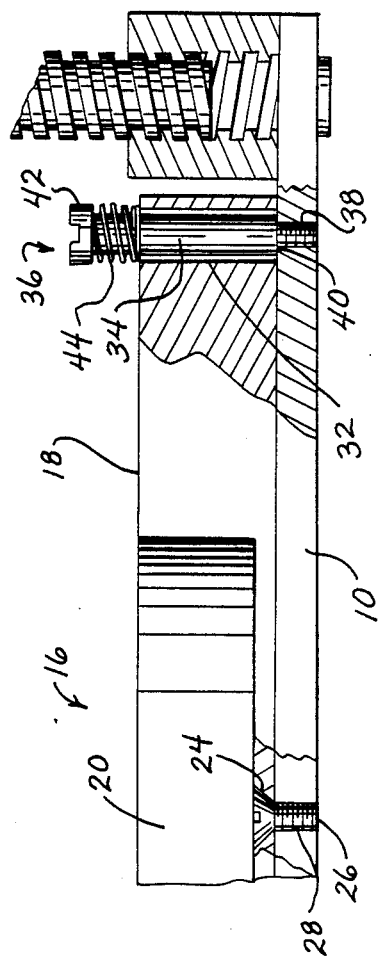

4,975,933

BOW-TIE X-RAY FILTER ASSEMBLY FOR DUAL ENERGY TOMOGRAPHY

BACKGROUND OF THE INVENTION

This invention relates to x-ray filters for controlling the energy of an x-ray beam and specifically to filters used in x-ray computed tomography systems for making dual energy measurements.

Computed tomography (CT) systems typically include an x-ray source collimated to form a fan beam directed through an object to be imaged and received by an x-ray detector array. The x-ray source, the fan beam and detector array are orientated to lie within the x-y plane of a Cartesian coordinate system, termed the "imaging plane". The x-ray source and detector array may be rotated together on a gantry within the imaging plane, around the imaged object, and hence around the z-axis of the Cartesian coordinate system.

The detector array is comprised of detector elements each of which measures the intensity of transmitted radiation along a ray path projected from the x-ray source to that particular detector element. At each gantry angle a projection is acquired comprised of intensity signals from each of the detector elements. The gantry is then rotated to a new gantry angle and the process is repeated to collect an number of projections along a number of gantry angles to form a tomographic projection set. Each acquired tomographic projection set may be stored in numerical form for later computer processing to reconstruct a cross sectional image according to algorithms known in the art. The reconstructed image may be displayed on a conventional CRT tube or may be converted to a film record by means of a computer controlled camera.

The x-ray source is typically comprised of an evacuated glass x-ray tube containing an anode and a cathode. X-rays are produced when electrons from the cathode are accelerated against a focal spot on the anode by means of a high voltage across the anode and cathode.

The spectrum of the x-rays produced encompasses a band of radiation of different frequencies and hence different energies. The short wavelength radiation of higher energy is referred to as "hard" x-ray radiation and the longer wavelength radiation of lower energy is referred to as "soft" x-ray radiation. The very lowest energy x-rays are almost entirely absorbed by the body and therefore provide little contribution to the x-ray image. Nevertheless, these soft x-rays contribute to the total exposure of the patient to harmful ionizing radiation. Accordingly, these rays are usually removed by a filter incorporated into the x-ray tube, as is known in the art.

The x-rays emitted by the x-ray tube may be subjected to two additional filters, a "spectral" filter and an "attenuation" filter.

The spectral filter may be a molybdenum strip which serves to harden the x-ray beam by further removing longer wavelength, lower energy x-rays. This spectral filter may be moved in and out of the beam of x-rays and hence provides the ability to image an object with x-ray beams of different spectral composition. The construction of x-ray images from two or more images taken with x-ray beams of different spectral composition is termed "dual energy scanning" and finds considerable use in the imaging of soft tissue where single energy scanning may only provide limited contrast. The spectral filter may be equipped with a track or hinge to permit its introduction and removal from the x-ray beam.

In addition to the spectral filter, the x-rays may be subjected to an attenuation filter. The attenuation filter is ordinarily a synthetic polymer such as Teflon having an x-ray absorption spectral characteristic near to that of water and hence the human body. This filter is not intended to adjust the spectral characteristics of the x-ray beam but rather to compensate for the variation in thickness of the imaged body The x-rays that pass through the center of the imaged body, ordinarily the thickest part, are least attenuated by this filter whereas the x-rays passing through the edges of the imaged body, ordinarily the thinnest part are more attenuated by this filter. The x-rays that are not intercepted by the body at all are maximally attenuated by this filter, ideally by an amount equal to that of the x-rays passing through the center of the body. The result of this selective attenuation is that the x-rays striking the Ct x-ray detectors are of similar energy and centered around the middle of the detector's sensitivity. The attenuation filter therefore may allow the use of more sensitive x-ray detectors reducing the range of x-ray energies.

For purposes of calibration it is ordinarily desirable that the attenuation filter may be removed from the path of the x-ray beam. This may be accomplished by positioning the attenuation filter on a movable track.

As mentioned, the attenuation filter may be constructed of a synthetic polymer such as Teflon so as to closely match the absorption characteristics of the imaged body. Although the absorption characteristics of such polymers may be relatively stable, under continued x-ray exposure the mechanical characteristics of the polymer change. The color of the material may darken and cracks may develop. The discontinuity of the x-ray beam introduced by the cracks may cause severe image artifacts and thus require the replacement of the filter. Such replacement may be both inconvenient and costly.

SUMMARY OF THE INVENTION

Although the applicant does not wish to be bound by a particular theory, it is believed that the cracking of the attenuation filter under continued use is caused by a combination of the embrittlement of the polymer of the attenuation filter through a breaking down of the polymer molecules by the x-ray beam, together with stresses set up between the attenuation filter and its support as they expand from the heat of the adjacent x-ray tube.

According to the present invention, therefore, the attenuation filter is mounted to reduce expansion induced stress. Specifically, the filter element for the attenuation filter is attached to a movable support plate for positioning the filter element within the x-ray beam. The center of the filter element is affixed to the support plate but the ends are attached to slide with changes in temperature and thus with changes in the dimensions of the filter element and the support plate.

In one embodiment, the ends of the filter element are fitted with holes and are held with a fastener having a shank diameter less than the diameter of the holes. The difference between the shank and hole diameter is equal to a predetermined expansion distance. The filter element is held against the support plate by a compression spring positioned between the head of the fastener and the filter.

It is one object of the invention to permit the ends of the filter element to slide as the filter element expands with respect to the support plate thus avoiding the stress that might cause the filter element to fracture as it becomes brittle with more x-ray exposure. The compression spring pushes the filter against the surface of the support plate but permits the filter to slide along the surface of the support plate as it expands.

It is another object of the invention to reduce image artifacts caused by shifting of the filter. The fixing of the filter along its center line permits the expansion of the filter toward either end without shifting of the entire filter toward either end. In one embodiment, the center of the filter element is attached to the support plate by means of an attachment wall. A hole in the attachment wall prevents the formation of stresses on the attachment as a result of expansion of the filter element in a direction perpendicular to its two ends.

In yet another embodiment, a second filter is attached to the support plate so that at a first support plate position the x-ray beam is attenuated by both the first and second filter element and at a second support plate position the x-ray beam is attenuated by only one filter element. The second filter is attached to the support plate so as to tension the first filter with relative expansion of the support plate.

It is thus another object of the invention to provide a method of incorporating the spectral filter with the attenuation filter so as to provide positive positioning of both. The tensioning of the spectral filter upon relative expansion of the support plate ensures that the spectral filter is not place under compression when cool which might lead to bucking. The spectral filter is fixed with respect to the attenuation filter and the entire filter assembly is moved in and out of the x-ray beam providing more accurate positioning of the spectral filter.

Other objects and advantages besides those discussed above shall be apparent to those experienced in the art from the description of a preferred embodiment of the invention which follows. In the description, reference is made to the accompanying drawings, which form a part hereof, and which illustrate one example of the invention. Such example, however, is not exhaustive of the various alternative forms of the invention, and therefore reference is made to the claims which follow the description for determining the scope of the invention.

BRIEF DESCRIPTION OF THE DRAWINGS

FIG. 2 is a partial cutaway plan view of the filter assembly showing the mounting of the attenuation filter to the support plate; and FIG. 3 is a plan view similar to that of FIG. 2, showing the mounting of the filter assembly on the drive mechanism for moving the filter assembly within the x-ray beam.

DETAILED DESCRIPTION OF THE PREFERRED EMBODIMENTS

Figure 1:
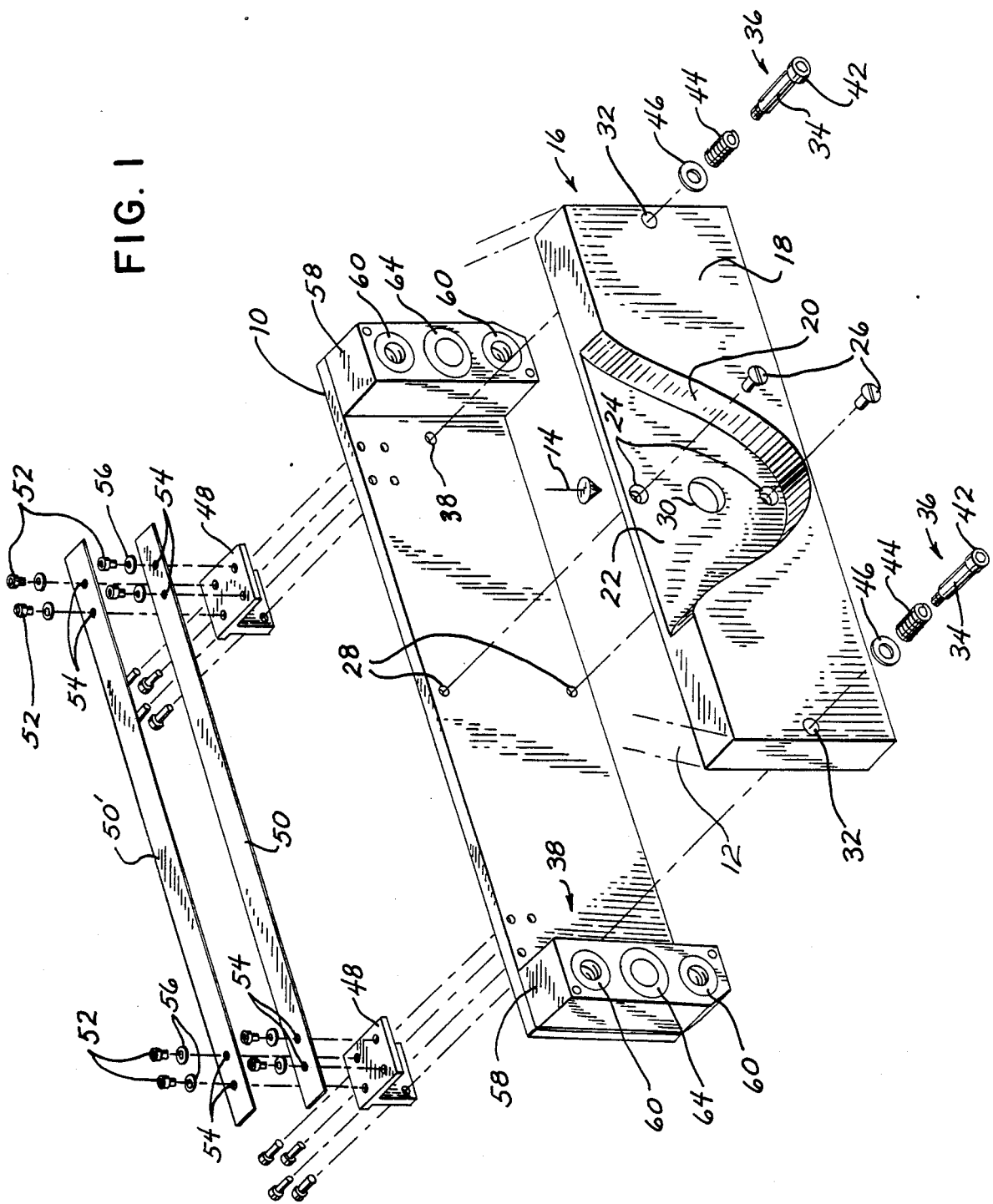
FIG. 1 is an exploded perspective view of the filter assembly showing the relative positions of the attenuation filter, the support plate and the spectral filters.

Referring to FIG. 1, a generally rectangular support plate 10 is positioned edgewise to a fan bean of x-rays 12 radiating vertically along axis 14. Attached to one face of the support plate 10 is an attenuation filter 16 comprised of a corresponding rectangular filter block 18 of Teflon. It will be apparent to those of ordinary skill in the art that other similar materials may be used for the attenuation filter 16. In the exposed face of the filter block 18 is a downward extending saddle notch 20 centered within the filter block 18 but less than the full width of the filter block 18 so as to leave intact a supporting wall 22. The saddle notch 20 reduces the thickness of the attenuation filter 16 along the path of the projected fan beam of x-rays 12 so that the thickness of the attenuation filter 16 correspond inversely to the thickness of a typical object being imaged (not shown). That is, the attenuation filter 16 is thinnest in the center to attenuate least those x-rays 12 that will pass through the thickest portion of the imaged object, and thickest at either edge to attenuate most the x-rays 12 which pass without any attenuation on either side of the imaged object. As mentioned above, the purpose of the attenuation filter 16 is to equalize, approximately, the intensity of the x-rays 12 received by a CT detector and hence to permit improved detector sensitivity.

The supporting wall 22 exposed by the saddle notch 20 contains two vertically disposed countersunk holes 24. Referring both to FIG. 1 and 2, the attenuation filter 16 is attached to the support plate 10 by means of flathead machine screws 26 fitted within countersunk holes 24 and received by corresponding tapped holes 28 at the center of the support plate 10. The attenuation filter 16 is thus fixed to the support plate 10 along the vertical line of symmetry of the support plate 10 and the attenuation filter 16. The interfitting faces of the flathead fasteners 26 and the countersunk holes 24 in the supporting wall 22 serve to prevent the shifting of the center of the attenuation filter 16 with respect to the support plate 10.

During use of the CT machine, the x-ray tube (not shown) releases considerable heat, heating the attenuation filter 16 and support plate 10 by up to 50° F. above the ordinary room temperature. The expansion of the attenuation filter 16 will differ from that of the support plate 10 depending on the materials from which each is constructed. With a Teflon attenuation filter and an aluminum support plate, the coefficient of expansion are approximately $80 \times 10^{-6}$ inches/inch-°F. and $13 \times 10^{-6}$ inches/inch-°F. respectively. The difference in expansion over 50° F. will therefore be approximately 3 thousandths of an inch per inch of material.

A stress relief hole 30 is cut in the supporting wall 22 of the attenuation filter 16 between the countersunk holes 28 to relieve stress caused by vertical expansion of the filter block 18 and the supporting wall 22 as it is heated by the adjacent x-ray tube (not shown). The distance between the mounting points of the supporting wall 24, i.e. the distance between the countersunk holes 24 is approximately 2 inches and hence 6 thousandths of an inch of expansion is accommodated by the stress relief hole 30. The stress relief hole deforms from a circle to an ellipse to prevent buckling of the supporting wall between the countersunk holes 24 with relative expansion of the filter block 18 on the support plate 28.

Horizontal expansion of the filter block 18 is considerably greater than the vertical expansion, described above, as a result of the greater length than height of the filter block 18. For example, the length of the filter block may be 10 inches and hence approximately 30 thousandths of an inch of horizontal expansion may be expected with the previously described conditions and materials.

This horizontal expansion of the filter block 18 is accommodated in a different manner than the vertical expansion. Oversized holes 32 are drilled through the face of each end of the filter block 18 to permit the insertion of the shank 34 of shoulder screws 36 which are received by corresponding tapped holes 38 in the face of the support plate 10 at either end of the support plate 10. The shoulder screws 36 are sized so that when the shoulder 40 of the shoulder screws 36 abut the face of the support plate 10, the shank 34 of the shoulder screws 36 extends beyond the outer face of the filter block 18 and the heads 2 of the shoulder screws 36 are displaced from the outer face of the filter block 18. A compression spring 44 is placed between the head 42 of each shoulder screw 36 and the outer face of the filter block 18. The compression spring 44 is sized so that it is compressed when the shoulder screw 36 is fully engaged with the support plate 10 and hence the compression spring 44 exerts an inward force on the filter block 18 holding it against the support plate 10. A washer 46 is placed between the compression spring 44 and the filter block 18 to spread the force of the compression spring 44 and reduce any cold flow of the material of the filter block 18.

The oversized holes 32 are of greater diameter than the shanks 34 of the shoulder screws 36 by approximately 60 thousandths of an inch to accommodate the 30 thousandths of an inch expansion of the filter block 18 along its horizontal dimension of approximately 10 inches. The compression spring 44 exerts only a normal force on the filter block 18 and hence does not resist the expansion of the attenuation filter 16 but affects only the sliding friction between the attenuation filter 16 and the support plate 10. This sliding friction is ordinarily low.

Referring again to FIG. 1, two T-brackets 48 are attached to the top edge of either end of the support plate 10 by means of a vertical leg of the T-bracket 48. The two horizontal arms of each T-bracket 48 each support one end of two parallel metallic filter strips 50 and 50' used as spectral filters. The ends of the filter strips 50 and 50' are secured to the horizontal arms of the T-brackets 48 by means of two machine screws 52 passing through holes 54 in the ends of the filter strips 50 and 50', and the horizontal arms of the T-brackets 48, and are secured with lock washers 56. The filter strips 50 and 50' are given a slight tension during assembly at room temperature to prevent buckling in cooler environments.

The filter strips 50 and 50' may be formed of molybdenum and will have a lower coefficient of expansion that an aluminum support plate 10. Specifically, the coefficient of expansion of molybdenum is approximately $3 \times 10^{-6}$ inches/inch-°F. versus $13 \times 10^{-6}$ inches/inch-°F. for an aluminum support plate 10. The difference in expansion over 50° F. will be approximately 0.5 thousandths of an inch per inch of material.

This expansion is accommodated by ensuring that the filter strips 50 and 50' do not slip with respect to the support plate 10 as both are heated and cooled and hence that the filter strips 50 and 50' are constantly in tension. Under tension, the filter strips 50 and 50' will not buckle. Unlike the polymer material of the attenuation filter 16, the metal filter strips 50 and 50' are not significantly embrittled with x-ray exposure and hence small amounts of stress may be accommodated.

One filter strip 50 is positioned above the attenuation filter 16 so as to shield one half of the attenuation filter's thickness from exposure by the x-ray fan beam 12. The other filter strip 50' extends from the rear of the support plate 10 away from the attenuation filter 16 and over unobstructed space. This configuration permits selective combinations of the attenuation filter 16 and the filter strips 50 and 50' as will be described below.

Referring to FIG. 1, pillow blocks 58 are attached to the face of support plate 10 at either end of support plate 10 beyond the extent of the filter block 18. Positioned within holes in the pillow blocks 58 at the corners of the support plate 10 are threaded inserts 60 which receive leads screws 62 as will be described later. Also within each the pillow block 58 centered between the threaded inserts 60 is a linear bearing 64 which receives a guide shaft 66 on which the pillow blocks 58 and the support plate 10 may move.

Referring now to FIGS. 2 and 3, lead screws 62 corresponding to the positions of threaded inserts 60 project from a motor drive plate 68 aligned with and parallel to the support plate 10. The lead screws are supported on the motor drive plate 68 by bearings 70 and are received by each of the threaded inserts 60. Two guide shafts 66 (only partially visible in FIG. 3) are similarly received by the linear bearings 64 and hold the weight of the support plate 10 as it moves toward and away from the motor drive plate 68 with motion of the lead screws 62.

The lead screws 62 are moved synchronously to ensure positive and parallel motion of the support plate 10 with respect to the motor drive plate 68 and the area of the fan beam of x-rays 12. This motion is accomplished by means of sprocket wheels 72 attached to each of the lead screw 52 near the motor drive plate 68 and connected together by a loop of roller chain 74. A drive sprocket wheel 76 is attached to a shaft of a stepper motor 78 which may be moved along the motor drive plate 68 by means of adjustment bolts 80 so as to remove any slack from the loop of roller chain 74 as is generally understood in the art.

The stepper motor 78 is controlled by a solid state stepper motor controller 82 which respond to digital signals, indicating direction and step number of steps, to move the shaft of the stepper motor 78 a certain number of degrees in either direction. The relative movement of the support plate 10 and hence the attenuation filter 16 and the filter strips 50 and 50' may be calculated from the pitch of the lead screws 62 and the number of degrees stepped by the stepping motor 78. The absolute position of the support plate 10 is determined by turning the lead screws 62 so as to draw the support plate 10 toward the motor drive plate 68 until the plunger of a limit switch 82 attached to the motor drive plate 68 is depressed by the face of the attenuation filter 16 facing the motor support plate 68. The depression of the plunger of the limit switch 82 indicates that the support plate 10 is in a known location. Future positions of the support plate 10 then may be determined by tracking the subsequent relative movements of the stepper motor 78.

Referring still to FIG. 3, the support plate 10 may be positioned in one of four locations with respect to the fan beam of x-rays 12. In the first location, the support plate 10 is furthest from the motor drive plate 68 and Region A is aligned with the fan beam 12 so that neither the attenuation filter 16 nor either filter strip 50 or 50' intercepts the fan beam 12. In the second location, the support plate 10 moves closer to the motor drive plate 68 so that Region B is aligned with the fan beam 12 and the attenuation filter 16 alone is in the path of the fan beam 12. In the third location, the support plate 10 moves yet closer to the motor drive plate 68 so that Region C is aligned with the fan beam 12 and both the attenuation filter 16 and a filter strip 50 are in the path of the fan beam 12. Finally, in the fourth location, the support plate 10 moves further toward the motor drive plate 68 so that only the filter strip 50' is in the path of the fan beam 12.

Thus the stepper motor 78 may be used to vary the filtration of the x-ray fan beam 12 by moving the support plate 10 appropriately.

The above description has been that of a preferred embodiment of the present invention. It will occur to those who practice the art that many modifications may be made without departing from the spirit and scope of the invention. For example, the attenuation filter 16, the filter strips 50 and 50' and the support plate 10 may be constructed of other materials as known in the art with different coefficients of expansion than those described herein. In order to apprise the public of the various embodiments that may fall within the scope of the invention, the following claims are made.

I claim:

1. In a computed tomography system having an x-ray source for projecting a collimated beam of x-rays along a projection axis, a filter assembly comprising:
   a filter element for attenuating the x-ray beam and having a center axis parallel with the projection axis and two ends disposed on either side of the center axis;
   a movable support plate for positioning the center axis of the filter element within the x-ray beam;
   center fastening means for fixedly attaching the filter element along its center axis to the support plate; and
   end attachment means for slidably attaching the ends of the filter element to each end to the support plate.

2. The filter assembly of claim 1 wherein the filter element includes holes in either end and the end attachment means comprise:
   a fastener having a shank, and at one end a head, the shank having a diameter less than the diameter of the holes by a predetermined expansion distance, the shank fitting through the holes and being received by the movable support plate for retaining the ends of the filter between a surface of the head and a surface of the movable support plate; and
   a compression spring means positioned between the head and the filter for slidably holding the the filter against the support plate.

3. The filter assembly of claim 1 wherein the filter element is comprised of a synthetic polymer.

4. The filter assembly of claim 1 wherein the filter element includes a support wall along its center line and there is a hole in the support wall to permit deformation of the support wall with expansion.

5. In a computed tomography system having an x-ray source for projecting a collimated beam of x-rays along a projection axis, a filter assembly comprising:
   a first filter element for attenuating the x-ray beam and having a center axis parallel with the projection axis and two ends disposed on either side of the center axis;
   a movable support plate for positioning the center axis of the first filter element within the x-ray beam;
   center fastening means for fixedly attaching the first filter element along its center axis to the support plate; and
   end attachment means for slidably attaching the ends of the first filter element to each end to the support plate.
   a second filter element for attenuating the x-ray beam and positioned with respect to the first filter element so that at a first support plate position the x-ray beam is attenuated by both the first and second filter element and at a second support plate position the x-ray beam is attenuated by only one filter element; and
   tensioning means for attaching the ends of the second filter means to the support plate means so as to tension the second filter means with relative expansion of the support plate means.

6. The filter assembly of claim 5 wherein the second filter means is a metallic strip.

* * * * *